United States Patent
Forster et al.

(10) Patent No.: US 10,251,683 B2
(45) Date of Patent: Apr. 9, 2019

(54) INTRAMEDULLARY NAIL

(71) Applicant: Vilex in Tennessee, Inc., McMinnville, TN (US)

(72) Inventors: Robert Forster, Palm City, FL (US); Abraham Lavi, Delray Beach, FL (US)

(73) Assignee: Vilex in Tennessee, Inc., McMinnville, TN (US)

( * ) Notice: Subject to any disclaimer, the term of this patent is extended or adjusted under 35 U.S.C. 154(b) by 0 days.

(21) Appl. No.: 15/612,273

(22) Filed: Jun. 2, 2017

(65) Prior Publication Data
US 2018/0125544 A1    May 10, 2018

Related U.S. Application Data

(63) Continuation of application No. 14/823,402, filed on Aug. 11, 2015, now abandoned.

(60) Provisional application No. 62/036,426, filed on Aug. 12, 2014, provisional application No. 62/039,275, filed on Aug. 19, 2014.

(51) Int. Cl.
*A61B 17/72*    (2006.01)

(52) U.S. Cl.
CPC .......... *A61B 17/72* (2013.01); *A61B 17/7233* (2013.01)

(58) Field of Classification Search
CPC ........................................ A61B 17/72–17/748
USPC ................................................... 606/62–68
See application file for complete search history.

(56) References Cited

U.S. PATENT DOCUMENTS

| | | | | |
|---|---|---|---|---|
| 2010/0063503 | A1* | 3/2010 | Dell'Oca | A61B 17/744 606/62 |
| 2010/0130978 | A1* | 5/2010 | Orbay | A61B 17/7241 606/62 |
| 2011/0190769 | A1* | 8/2011 | Haininger | A61B 17/72 606/64 |
| 2011/0218531 | A1* | 9/2011 | Orbay | A61B 17/56 606/62 |
| 2012/0226278 | A1* | 9/2012 | Nardini | A61B 17/7241 606/64 |

* cited by examiner

*Primary Examiner* — Nicholas J Plionis
(74) *Attorney, Agent, or Firm* — Barbara E. Johnson, Esq.

(57) ABSTRACT

A versatile intramedullary nail is constructed in two cooperating and optionally interlocking pieces, with a further optional annular restoration hub. The two cooperating pieces, when interlocked, approximate a long shaft, generally tubular in cross-section, with a recessed area on the male piece adapted to receive the annular restoration hub. The female piece is adapted to receive the flange of the male piece coaxially, and—unless a locking screw or bolt is inserted through the flange—the two pieces can rotate axially. Alternatively, the nail can be constructed of a single solid piece.

2 Claims, 3 Drawing Sheets

INTRAMEDULLARY NAIL

BACKGROUND AND CROSS REFERENCE

The present invention is a versatile nail for use in the intramedullary canal of the ulna or the fibula, and is a continuation of U.S. Ser. No. 14/823,402 filed 11 Aug. 2015, which claims priority to U.S. Patent Application Ser. Nos. 62/036,426 filed 12 Aug. 2014 and No. 62/039,275 filed 19 Aug. 2014, each of which is incorporated herein by reference.

FIELD OF THE INVENTION

Description of Related Art

Intramedullary nails are known in the art, and are widely used throughout the world to repair fractures or to reinforce bone shafts during and after surgery of various types. The intramedullary canal (synonymous with the marrow canal) is an ideal place for insertion of a support structure, because the relatively softer bone or marrow provides an easy implantation site, and intramedullary implants are less compromising to bone than other bone inserts. Traditional intramedullary nails or rods have typically been secured with locking bolts or screws to the adjacent bone, to prevent unwanted rotation, and a customary "cloverleaf" cross-sectional shape also prevents unwanted rotation of implants within the intramedullary canal.

One disadvantage of a traditional intramedullary nail inhered in its elongated length: surgical implantation was often complicated simply by the sheer size of the nail. Also, prior art intramedullary nails and rods were typically designed to be completely stationary within the bone, and hold the bone immobile-specifically not allowing motion within the bone but only at the adjacent joint. This invention is specifically designed to allow motion within a long bone in a controlled fashion, while providing stability in all planes and provide load sharing. Additionally the device may enable immediate rehabilitation to begin without the need for a period of immobilization to allow soft tissues to heal completely.

For example, during prior art distal radia-ulna joint fusion procedures intended to reduce pain due to arthritis or other deterioration, sometimes an osteotomy along the ulna was performed to restore range of motion otherwise lost by fusing the distal radia-ulna joint. However, having the ulna in two pieces, with only one end of each piece's being securely anchored, created problems of its own such as instability of the proximal ulna stump, even though the osteotomy did restore some range of motion after the fusion. A stationary intramedullary nail would have merely removed the range of motion restored by the ulna osteotomy. A need therefore remains for a versatile intramedullary nail which not only provides the traditional reinforcement function of a prior art intramedullary nail or rod, but also can restore range of motion to one or more joints adjacent to the implant, as needed.

SUMMARY OF THE INVENTION

In order to meet this need, the present invention is a versatile intramedullary nail constructed in one piece or in two cooperating and optionally interlocking pieces, with a further optional truncated annular restoration hub. The two cooperating pieces, when interlocked, approximate a long shaft, generally tubular in cross-section, with a recessed area on the male piece adapted to receive the truncated annular restoration hub. The female piece is adapted to receive the flange of the male piece coaxially, and—unless a locking screw or bolt is inserted through the flange—the two pieces can rotate axially and independently of each other. (Alternatively, the aforesaid nail structures can be manufactured as a single piece and, in such case, no interior rotation will take place.). Bolt or screw holes near the ends of either piece allow selective anchoring of either or both pieces to the adjacent intramedullary bone. However, if the interconnected pieces are interlocked and only one piece is bolted or screwed to the adjacent intramedullary bone, the other piece can rotate freely within the intramedullary canal to restore range of motion to an adjacent joint. Conversely, if the interconnected pieces are each bolted or screwed to their respective bone but the interconnection is NOT interlocked, then the two pieces maintain their lengthwise rigidity but can rotate axially depending on exertion from an adjacent joint. The present intramedullary nail or plate is particularly suited for use within the ulna or fibula, especially after wrist or even ankle joint fusion creates a need for improved range of motion in the hand or foot.

DETAILED DESCRIPTION OF THE INVENTION

The present invention is a versatile intramedullary nail constructed in one piece or in two cooperating and optionally interlocking pieces, with a further optional truncated annular restoration hub. The two cooperating pieces, when interlocked, approximate a long shaft, generally tubular in cross-section, with a recessed area on the male piece adapted to receive the truncated annular restoration hub. The female piece is adapted to receive the flange of the male piece coaxially, and—unless a locking screw or bolt is inserted through the flange—the two pieces can rotate axially and independently of each other. (Alternatively, the aforesaid nail structures can be manufactured as a single piece and, in such case, no interior rotation will take place.) Bolt or screw holes near the ends of either piece allow selective anchoring of either or both pieces to the adjacent intramedullary bone. When both pieces of the nail are anchored (via bolt or screw) to the adjacent bone, the two pieces can rotate axially due to the configuration by which the two shafts cooperate. However, if the interconnected pieces are interlocked and only one piece is bolted or screwed to the adjacent intramedullary bone, the other piece can rotate freely within the intramedullary canal itself, to restore range of motion to an adjacent joint via relative axial rotation between two portions of the same bone. The present intramedullary nail is particularly suited for use within the ulna or fibula, especially after wrist or even ankle joint fusion creates a need for improved range of motion in the wrist or ankle.

Figure 1:
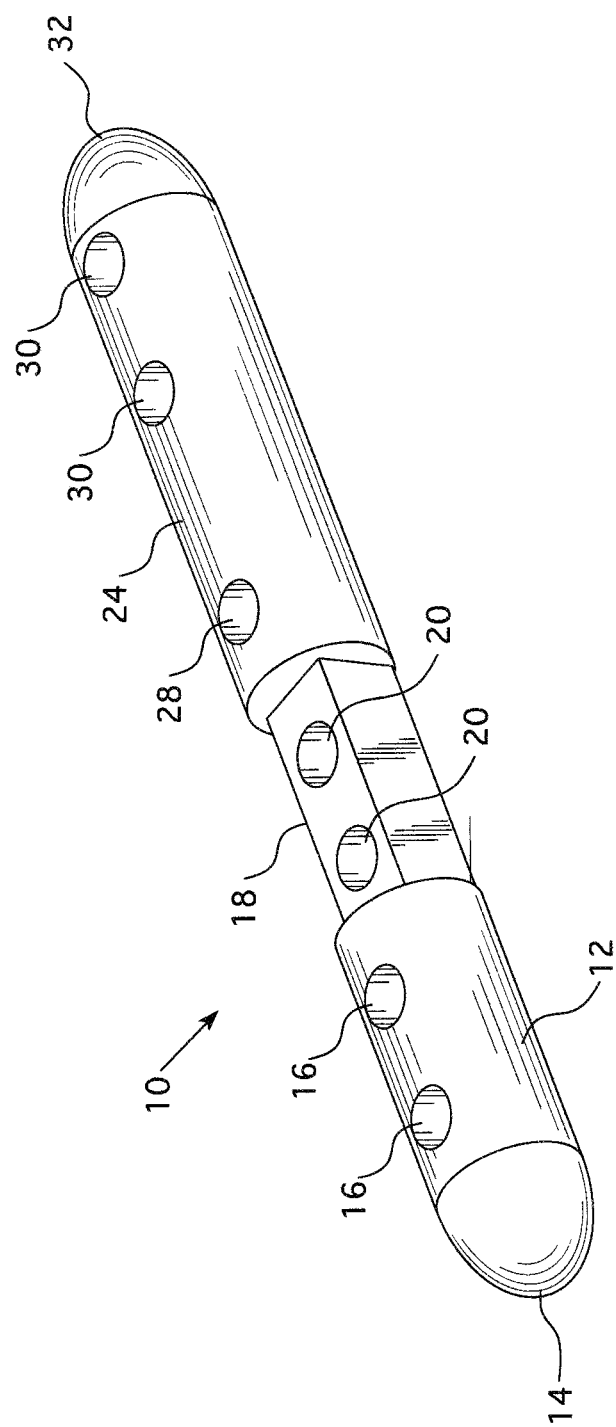
FIG. 1 is a perspective view of the intramedullary nail of the present invention, shown without the restoration hub.

Referring now to FIG. 1, an intramedullary nail according to the present invention is shown in perspective view. The intramedullary nail 10 contains two portions, namely, the distal stem 12 (having a distal stem end 14 which is typically but not necessarily smoothly curved) and the free proximal stem 24 having a free proximal stem end 32 (also generally smoothly curved). The distal stem 12 and the proximal stem 24 are constructed as a single piece with a hub core 18. The hub core 18 has less width than the diameter of the distal stem 12 and typically has smooth rectangular sides as shown in FIG. 1. The distal stem 12 contains distal stem anchor holes 16 and the hub core 18 contains hub core anchor holes 20. The free proximal stem 24 contains stem anchor holes 30 and a locking hole 28. As is the case throughout this specification, anchor holes may be either holes for bolts or threaded holes for screws—the purpose of the anchor hole is a recess or void adapted to receive a fastening device suitable for interconnecting the intramedullary nail to adjacent bone. The free proximal stem also contains an axial hinge anchor hole 28, explained further below.

Figure 2:
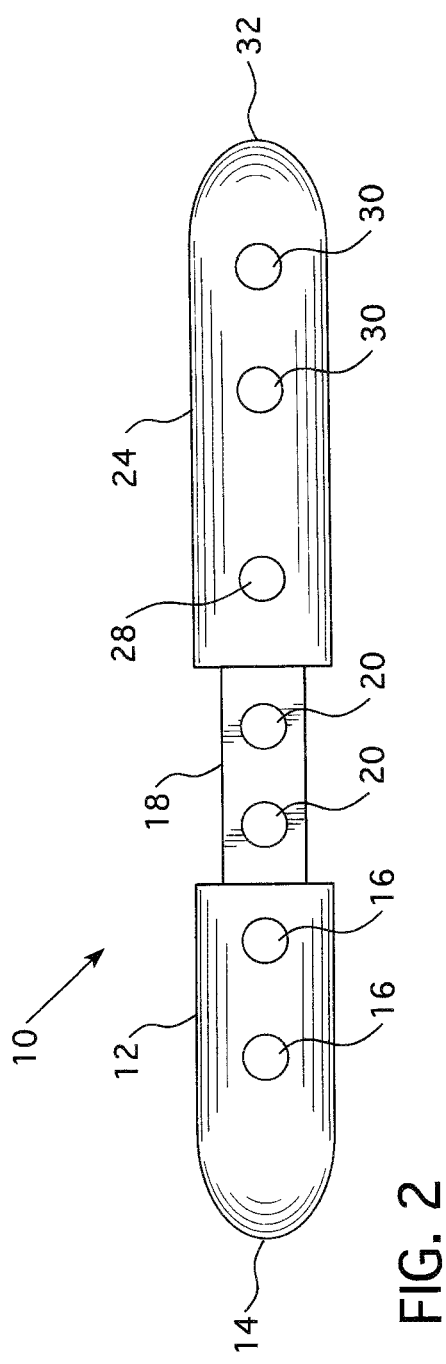
FIG. 2 is a plan view of the intramedullary nail of FIG. 1.
Figure 3:
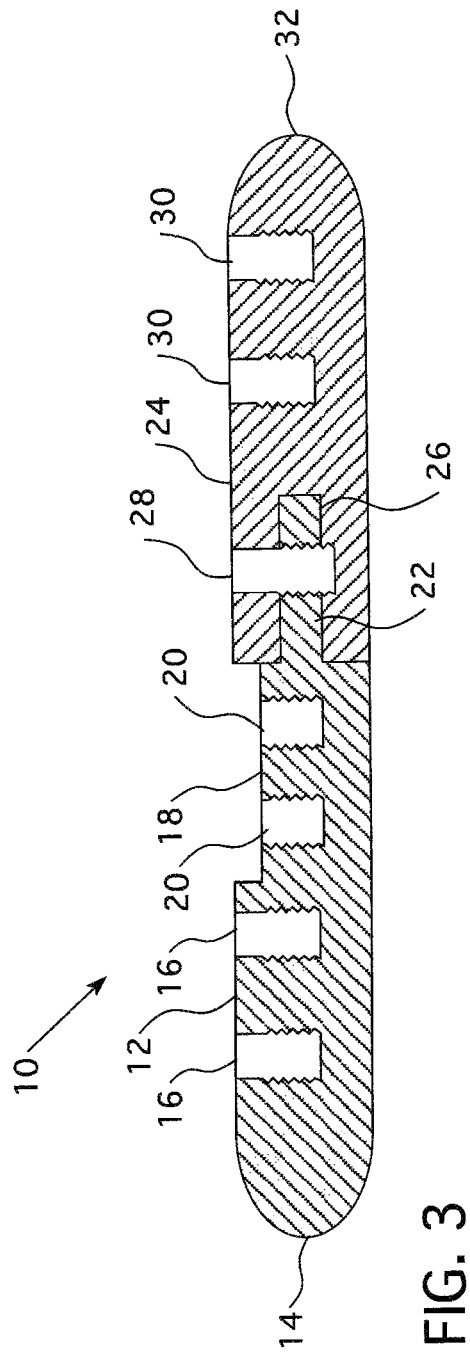
FIG. 3 is a side sectional view of the intramedullary nail of FIG. 1.

Referring now to FIG. 2, the same structures of FIG. 1 may be seen in plan view, and in FIG. 3 not only does it become apparent that the hub core 18 is inset (with respect to its distal stem) only on three sides, but that there is an axial hinge post 22 on the distal stem 12. FIG. 3 also shows the axial hinge receptacle 26 in the free proximal stem 24, which receptacle is cylindrical and only slightly larger than the cylindrical axial hinge post 22. The concentric cooperation of the axial hinge post 22 within the axial hinge receptacle 26 means that the distal stem 12 and the free proximal stem 24 can rotate freely about each others' axes except when a bolt or screw (not shown) is present in the axial hinge anchor hole 28. By the way, the reason the free proximal stem 24 is called "free" is not that it cannot be anchored as desired, but because it is "free" of the hub core present on the other piece of the intramedullary nail. Incidentally, and as is explained elsewhere in this patent application, the "free proximal stem" is sometimes left unanchored within its intramedullary canal, so as to be able to rotate therein, but an unanchored distal stem can also rotate within the intramedullary canal, so "free" in "free proximal stem" should not be assumed to mean rotatable, per se.

Figure 4:
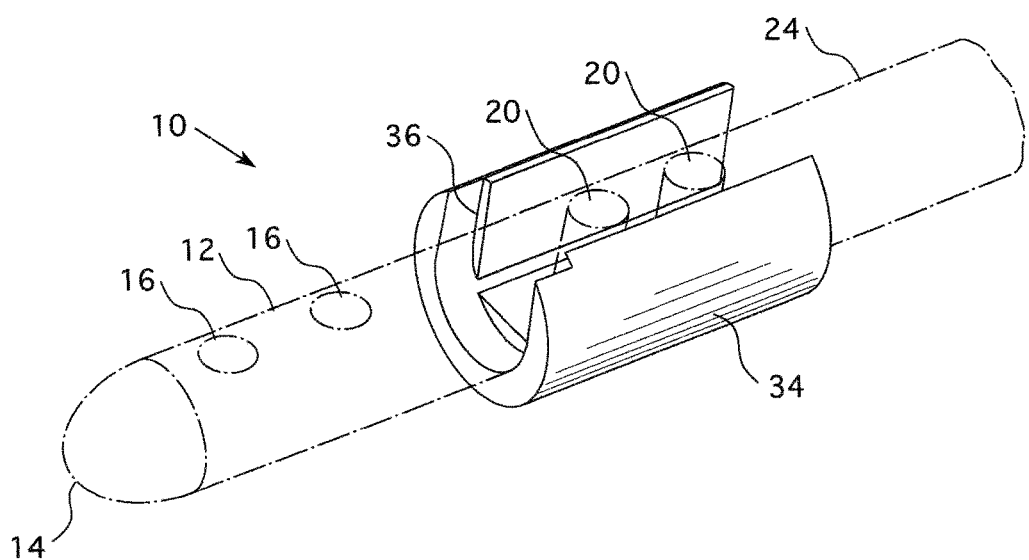
FIG. 4 is a partial plan view of the intramedullary nail of FIG. 1, shown with the restoration hub in place.
Figure 5:
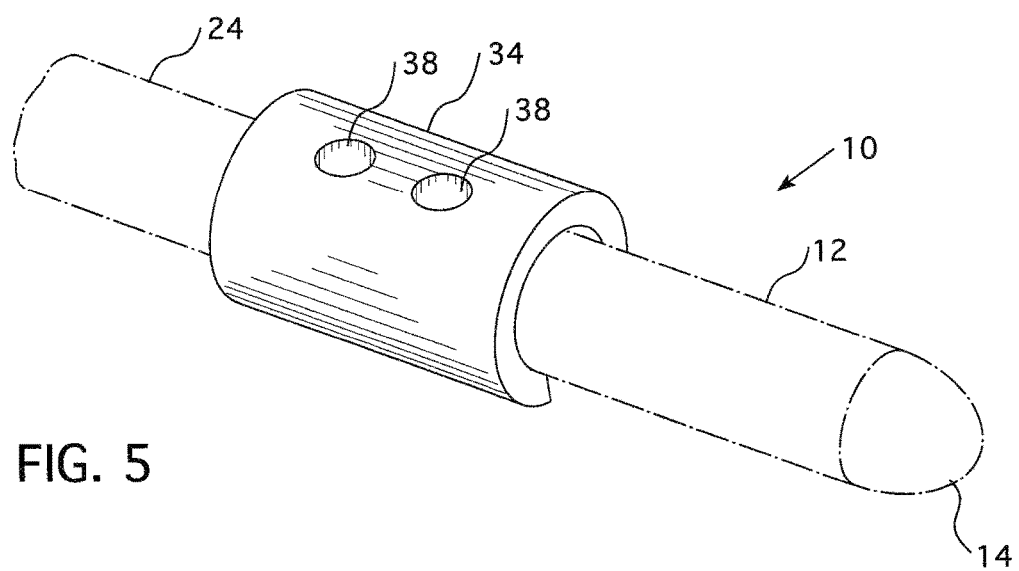
FIG. 5 is a perspective view of the intramedullary nail and restoration hub of FIG. 4, inverted 180 degrees to show the anchor holes in the restoration hub.

When the present intramedullary nail is used to restore an ulna osteotomy (such as has been performed in the past to restore range of motion lost to distal radia-ulna joint fusion) in order to implant the present intramedullary nail it is customary for a portion of the shaft of the ulna to be removed-anywhere from about 10 to 20 millimeters of bone or so. Removal of a portion of the bone greatly facilitations the implantation of the intramedullary nail pieces at the cut ends of the bone. However, the present intramedullary nail is by definition narrower than the bone into which it is implanted, because the implant must fit in the intramedullary canal inside the bone. Therefore, the intramedullary nail, being smaller in diameter than the bone diameter, does not completely fill the excised 10 to 20 millimeter bone segment—and providing that filling function is the purpose of the restoration hub capsule 34 shown in FIG. 4. The restoration hub capsule 34 is designed to be longer than the length dimension of the hub core 18, with interior diameters designed to match the shape and position of the hub core 18 (see restoration hub capsule interior flange 36) and the larger diameters of the distal stem and free proximal stem. In other words, as shown in FIG. 4 the interior diameter of the restoration hub capsule 34 is designed to mate both with the hub core 18 and with the larger-diameter exterior of the distal stem 12 or the free proximal stem 24. FIG. 5 shows the assembly of FIG. 4 inverted by 180 degrees, to show the restoration hub capsule anchor holes 38. The restoration hub capsule anchor holes 38 may be used to fasten (via one or two bolts or screws) the restoration hub capsule to the two-part intramedullary nail. The use of the restoration hub capsule is optional. The present invention will work without the restoration hub capsule. In an ulna implantation, however, the restoration hub capsule keeps the patient from probing and feeling—or even seeing—an indentation in the ulna and thus in the forearm, were the restoration hub capsule not in position. Imagine touching a forearm with the hand-without the restoration hub capsule, one would feel sharp ridges through the skin, about a third of the way up the forearm from the wrist, and such ridges would lead to great patient dissatisfaction. An additional benefit of the optional restoration hub capsule is minimizing longitudinal pistoning when the nail is inserted with one side not locked as previously described when used to restore forearm rotation after distal radius and ulna fusion.

In operation, the structures of FIGS. 1-5 provide the maximum versatility to the surgeon as is possible. If the distal stem 12 and the free proximal stem 24 are simply adjoined by bolt or screw via axial hinge anchor hole 28, the present invention functions as though it were a single piece intramedullary canal implant, whether further anchored with additional bolts or screws or not. Given the immediately previously described configuration of distal stem 12 and free proximal stem 24 affixed at the axial hinge anchor hole, if either but not both of the distal stem 12 or the free proximal stem 24 is affixed to its adjacent bone, the other stem will be able to rotate freely within its respective intramedullary canal as long as the axial hinge post and the axial hinge receptacle remain affixed together. However, even if both the distal stem 12 and the free proximal stem 24 are affixed to their adjacent bones via their respective anchor holes, as long as the axial hinge post 22 is left free to rotate within the axial hinge receptacle 26 (that is, there is no screw or bolt in axial hinge anchor hole 28) then the two pieces will be able to rotate axially. In an ulna restoration incident to wrist fusion, such axial rotation restores range of motion to the wrist and forearm as a result of one part of the ulna's being able to rotate axially vis a vis the other part.

Variations on the above combinations will be apparent to orthopedic surgeons accustomed to bone implants. For example, even though many anchor holes are provided in pairs (not the axial hinge anchor hole for obvious reasons), only one of the anchor holes needs to be used at a time, depending on accessibility issues and choice of bone for fixation. FIG. 3 shows screw threads within the anchor holes because threaded screw fasteners are generally better suited to the invention than true bolts, which would typically require a complete through hole with accompanying nut. Materials used to construct the pieces of the intramedullary nail shown in FIG. 1-5 are any materials-generally metals-suitable to bone implants within an animal or human subject, and such materials are well known in the art. However, in order to minimize friction during rotation, the interface between the axial hinge post 22 and the axial hinge receptacle 26 may be coated with a biocompatible composite material such as PEEK (polyaryletherketone) or UHMWPE (ulta high molecular weight polyethylene). Whereas a clear indication for the present intramedullary nail is the ulna, it is also suitable for use in the fibula and—because it is so versatile—the instant intramedullary nail can really be used in any desired intramedullary canal in which the surgeon wishes to add reinforcement to the bone. If desired, the intramedullary nail can be constructed with the axial hinge receptacle's being located in the distal stem rather than in the free proximal stem, but optimally the axial hinge receptacle is in the free proximal stem because the larger diameter of the free proximal stem provides greater structural stability despite the weakening void presence of the axial hinge receptacle.

Although the invention has been described as a two-piece device consisting of a distal and a proximal stem, another one-piece implementation is possible. FIG. 1 may be viewed as a one-piece device. The implanting procedure for the one piece-device is different from the two piece device. The one piece-device can accept a restoration hub at the hub core 18. The one piece implementation can function as a conventional intramedullary nail to reinforce the host bone when both ends are fixated to their respective adjacent bones. If only one end is fixated to its adjacent bone and the other end is not fixated but left free to rotate within the interamedullary canal, the device functions as an axial hinge. Furthermore, although the invention has been described with particularity above, with specific reference to structures, conformations, and functions, the invention is only to be limited insofar as is set forth in the accompanying claims.

The invention claimed is:

1. A method of treating a bone in an animal or human in need of treatment, comprising: selecting an in-line, two piece intramedullary nail consisting essentially of a first piece and a second piece, wherein at least one of said first piece or said second piece has a curved end surface and further wherein said first piece bears an axial hinge post which concentrically engages an axial hinge receptacle in said second piece with said first piece and said second piece being oriented to rotate only along an axial plane that retains said first and second piece in-line with one another, and further wherein each of said first piece and said second piece have at least one anchor hole therein and in addition also have at least one axial hinge locking hole therein, in addition to containing fastening devices which reside in and secure each of said anchor holes while leaving said at least one axial hinge locking hole of at least one of said first piece or said second piece empty, rendering said axial hinge post and said axial hinge receptacle free to rotate about one another, and implanting said in-line, two piece intramedullary nail within first and second bone segments to be joined wherein a direction of bone anastomosis of said first and second bone segments is in-line with said first and second piece and further wherein the resulting implanted axial hinge post and said axial hinge receptacle are free to rotate about one another after implantation is complete, concomitantly allowing axial rotation of said first and second bone segments relative to one another.

2. A method of treating an ulna having a shaft, in a human in need of treatment, comprising: selecting an in-line, two piece intramedullary nail consisting essentially of a first piece and a second piece, wherein at least one of said first piece or said second piece has a curved end surface and further wherein said first piece bears an axial hinge post which concentrically engages an axial hinge receptacle in said second piece with said first piece and said second piece being oriented to rotate only along an axial plane that retains said first and second piece in-line with one another, and further wherein each of said first piece and said second piece have at least one anchor hole therein and in addition also have at least one axial hinge locking hole therein, wherein said second piece has an anchor which extends into and through said axial hinge receptacle and wherein said nail contains at least one fastening device residing in at least one of said anchor holes, and further wherein at least one of said pieces contains no fastening device in any anchor hole, followed by incising and removing 10-20 mm of bone material from said shaft of said ulna followed by implanting said in-line, two piece intramedullary nail within first and second bone segments of the incised ulna shaft, to be rejoined in the same area where 10-20 mm of bone material was removed by attaching said nail to one of said first or second bone segments via said at least one fastening device, and placing a bone restoration hub over the intramedullary nail to fill the area of bone removal, wherein a direction of bone anastomosis of said first and second bone segments is in-line with said first and second piece and further wherein the resulting implanted nail is free to rotate within one of said first or second bone segments after implantation is complete, concomitantly allowing axial rotation of said first and second bone segments relative to one another and with said restoration hub limiting longitudinal pistoning of said two piece intramedullary nail within said first and second bone segments.

* * * * *